United States Patent [19]

Cavazza

[11] 4,338,931

[45] Jul. 13, 1982

[54] DEVICE FOR THE QUICK INHALATION OF DRUGS IN POWDER FORM BY HUMANS SUFFERING FROM ASTHMA

[76] Inventor: Claudio Cavazza, 35, Via Marocco, 00144 Rome, Italy

[21] Appl. No.: 144,016

[22] Filed: Apr. 28, 1980

[30] Foreign Application Priority Data

Apr. 27, 1979 [IT] Italy ................ 48883 A/79

[51] Int. Cl.³ .......................................... A61M 15/06
[52] U.S. Cl. ............................................. 128/203.15
[58] Field of Search ..................... 128/203.15, 203.23, 128/202.21, 266, 265, 203.21; 272/99 R

[56] References Cited

U.S. PATENT DOCUMENTS

| 515,637 | 2/1894 | Wilhide | 272/99 |
|---|---|---|---|
| 1,406,903 | 2/1922 | Rose | 128/265 |
| 2,307,986 | 1/1943 | Bolte et al. | 128/266 |
| 2,342,853 | 2/1944 | Furstenberg | 128/202.21 |
| 3,425,414 | 2/1969 | La Roche | 128/203.21 |
| 3,906,950 | 9/1975 | Cocozza | 128/203.21 |

FOREIGN PATENT DOCUMENTS 1436028 5/1976 United Kingdom ............. 128/266

Primary Examiner—Henry J. Recla
Attorney, Agent, or Firm—McGlew and Tuttle

[57] ABSTRACT

A device is disclosed for the inhalation of a drug in powder form contained in a capsule made of a pierceable material by humans suffering from asthma, which comprises two cylindrically-shaped members at least one of which is provided with hollow piercing means, the members being open-ended, matingly engaged and telescopically slidable into each other between a first position at which the capsule in its integral condition is positioned between the members, and a second position at which the capsule is pierced by said hollow piercing means in such a way that the suction exerted by the user allows the drug inhalation to take place.

4 Claims, 8 Drawing Figures

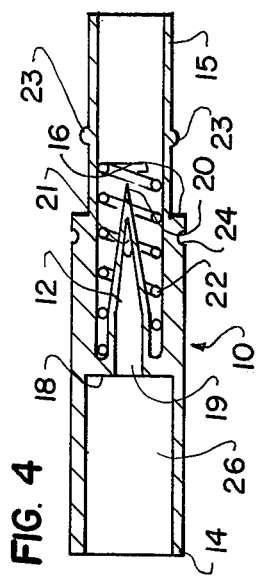
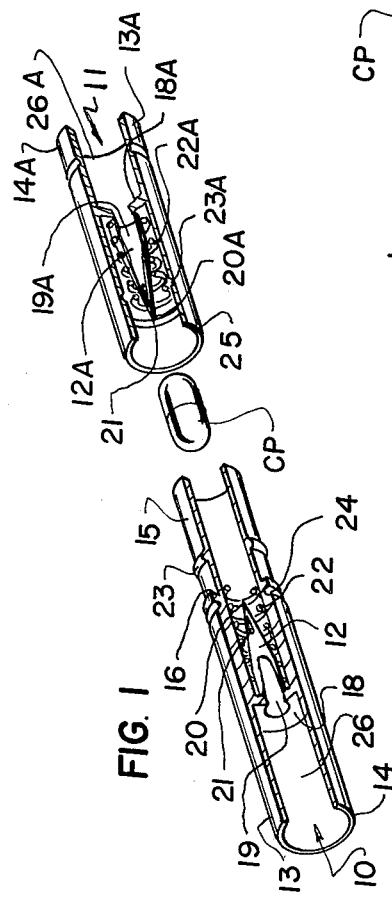
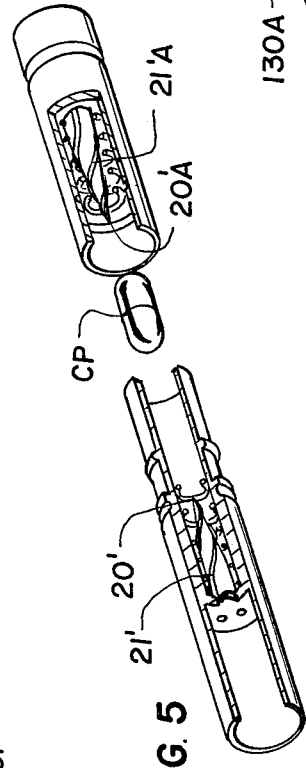
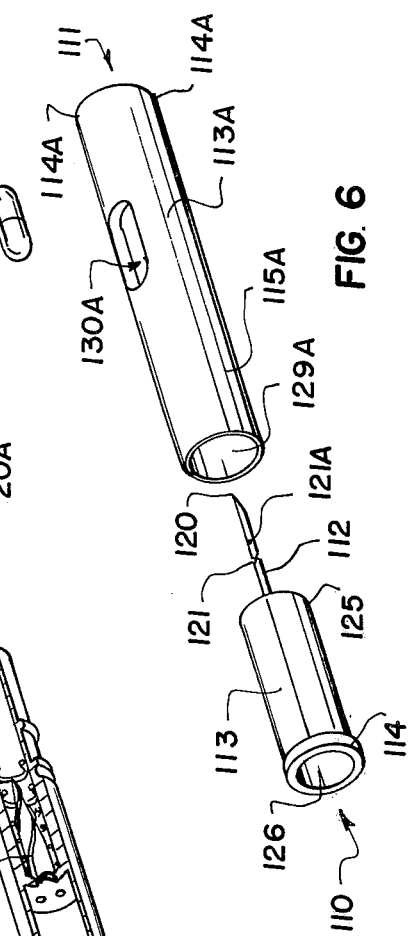
FIG. 4
FIG. 1
FIG. 5
FIG. 6

1

DEVICE FOR THE QUICK INHALATION OF DRUGS IN POWDER FORM BY HUMANS SUFFERING FROM ASTHMA

FIELD AND BACKGROUND OF THE INVENTION

The present invention relates to a device for the quick inhalation of drugs in powder form by humans suffering from asthma.

It is known that the drugs for treating asthma are inhaled and that, usually, inhalation must be repeated several times a day. Consequently, these drugs are normally sold in the form of ready-made pocket-size packs.

It is also known that the foregoing drugs have long since been marketed in the form of sprays, the therapeutically active agent being atomized in a gas, e.g. freon.

Recently, however, pharmaceutical compositions have been developed wherein the drug is in the form of a very fine powder contained in a cylindrically shaped, round-ended capsule made of a rigid, pierceable material, which have substituted the spray packs.

The drug is then inhaled by means of a device suitable for carrying out the steps of piercing the capsule at two or more points of the capsule and conveying through the pierced capsule an air stream which causes a suspension of fine drug particles in the air to be formed.

Such air stream is brought about by the patient who, after having introduced the inhalator into his mouth, draws in air.

To properly carry out the foregoing steps the inhalator must be provided with means suitable for piercing the capsule, drawing therein the air stream caused by the suction exerted by the user, and causing the suspension to leave the capsule and enter the user's mouth.

Several types of these inhalators at present on the market are, however, cumbersone, complicated and expensive. Consequently, these devices have to be re-used, whereas for reasons of hygiene and, particularly, owing to the difficulty of keeping the mouthpiece clean it would be proper and more convenient to have available inhalators which can be disposed of after one single use.

SUMMARY OF THE INVENTION

The object of the present invention is, therefore, to provide a highly effective inhalator which is also of simple construction and inexpensive and can be, consequently, disposed of along with the empty capsule, after a single use.

The inhalator of this invention essentially comprises two cylindrically-shaped members at least one of which is provided with hollow piercing means, the members being open-ended, matingly engaged and telescopically slidable into each other between a first position at which the capsule in its integral condition is positioned between the members, and a second position at which the capsule is pierced by said hollow piercing means in such a way that the suction exerted by the user allows the drug inhalation to take place.

The invention will now be described in more detail with reference to the attached drawings wherein two preferred embodiments of the inhalator according to this invention are disclosed.

BRIEF DESCRIPTION OF THE DRAWINGS

In the drawings:

FIG. 1 is an exploded, partly sectional view of a first embodiment of the device according to the invention;

FIG. 4 is an enlarged axial section of one of the two members of the device shown in FIG. 1;

FIG. 5 is a view similar to that of FIG. 1 showing a further embodiment of the device in FIG. 1;

FIG. 6 is a view similar to that of FIG. 1 showing another embodiment of the device of this invention;

DETAILED DESCRIPTION

Figure 2:
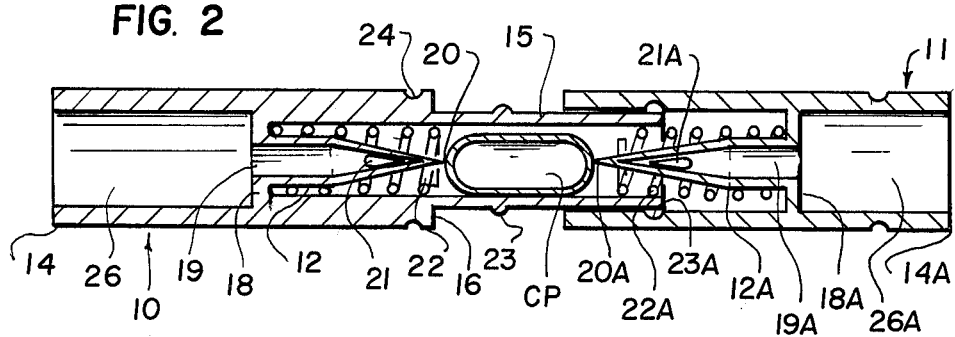
FIG. 2 is an axial sectional view of the device in FIG. 1, showing a capsule in its inserted position.

With specific reference to FIG. 1, according to a first embodiment of the device of this invention, it comprises a first, male member 10 and a second, female member 11, each member being provided with a hollow piercing element integral therewith, such elements being designated with the reference numerals 12 and 12A, respectively.

The member 10 consists essentially of a cylindrical body 13 having an outer end 14 and a forward sleeve 15 the diameter of which is smaller than that of the cylindrical body. Consequently, a collar 16 is formed along the joint line of the body 13 to the sleeve 15.

A collar 18 having a centrally-positioned passageway 19 is integral with the body 13. Collar 18 is also integral with the foregoing hollow piercing element 12 which is provided with a tip 20 presenting a number of tiny holes 21.

A spring coil 22, an end whereof is fastened to the collar 18, is positioned around the piercing element 12.

On the outer wall of the forward sleeve 15 an annular rib 23 having a rounded back is formed. On the outer wall of body 13, in proximity to the collar 16, there is an annular groove 24.

The member 11 is structured in a manner substantially identical to that of body 10, except that sleeve 15 is missing and that on its inner wall, in proximity to the end 25 thereof, there is an annular groove 23A. The parts of member 11 which are similar or identical to those of member 10 are designated with the same reference numerals to which a capital A has been added. So, the member 11 comprises a body 13A integral with a collar 18A having a centrally-positioned passageway 19A.

A hollow piercing element 12A is integral with the collar 18A and is provided with a tip 20A presenting all around a number of tiny holes A spring coil 22A one end whereof is secured to the collar 18A, is positioned around the hollow piercing element.

On the inner wall of body 13A is formed a round-bottomed annular groove 23A, distanced from the end 25 as equally as is the rib 23 from the collar 16 on member 10.

In operation:

The capsule CP is inserted into the sleeve 15 of the member 10 and the sleeve is fitted into an opening the end 25 of member 11, thus bringing the device in an position of FIG. 2. The members 10, 11 are then thrusted into each other until the edge of the end 25 of member 11 abuts against the collar 16 of member 10, thus reaching the position of FIG. 3. In this position, the piercing tips 20, 20A have pierced the opposite ends of capsule CP, in such a way that also the holes 21, 21A are inside the capsule.

Figure 3:
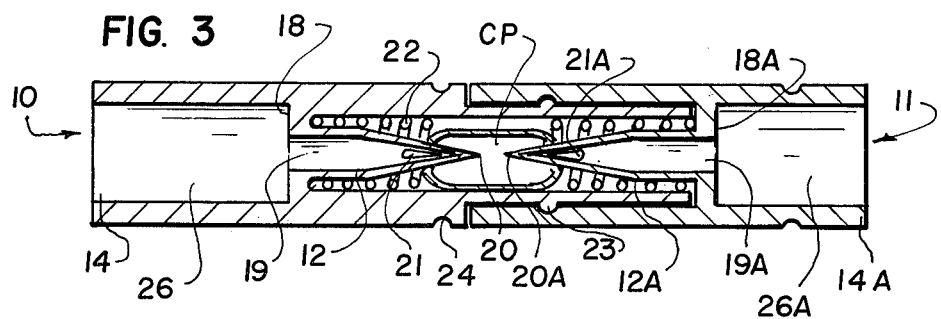
FIG. 3 is a view similar to that of FIG. 2, showing the pierced capsule.

It should be noted that in the position of FIG. 3 the outer rib 23 of the sleeve 15 of member 11 is received in the mating groove 23A of body 13A, thus holding members 10, 11 in mutual engagement and counteracting the action of springs 22, 22A which would separate them. The device as shown in FIG. 3 is thus ready for use. In order to inhale the drug in powder form contained in the capsule CP, the user will put into his mouth either one of the device ends, e.g. end 14, and draw in air through the opposite end 14A. Thus, the air drawn in through the end 14A will enter the capsule CP through the recess 26A of member 11, the opening 19A and the holes 21A of tip 20A of body 11, and will leave through the holes of tip 20, the opening 19, the recess 26 and the end 14 of member 10 to be eventually inhaled by the user.

Upon passage of the air stream through the capsule CP, owing to the air stream speed and the turbulences within the capsule brought about by the tips 20, 20A of piercing elements 12, 12A, all the powder contained in the capsule passes to suspension and is inhaled by the user.

The annular groove 24 plays an important role in allowing a correct positioning and proper operation of the inhalator to be achieved. In fact, in order to attain a proper inhalation, it is preferable that the outlet end of the device be positioned close to the throat or, anyhow, well inside the user's mouth. This is easily obtained by inserting into the mouth either the end 14 or the end 14A of the device until the incisors can grip the inhalator at the groove 24.

It should be noted that the springs 22, 22A could also be completely omitted in a disposable inhalator, because they function so as to allow the device reuse to be achieved, insofar as the springs eject the used capsule upon disengagement of members 10, 11 after use. However, because the springs 22, 22A can be made of plastic material, which is the material of choice for manufacturing the inhalator of this invention, and can be easily obtained when the members 10, 11 are molded, these spring do not significantly add to the overall cost of the inhalator.

FIG. 5 shows a variation of the device illustrated in FIGS. 1–3.

The difference resides in the fact that on the piercing tips 20', 20'A, in lieu of the two series of holes 21, 21A, there are some slots 21', 21'A having a helicoidal pattern. This arrangement aims at obtaining inside the capsule CP, upon inhalation, a more intense air turbulence which facilitates the suspension formation.

Because, apart from the foregoing particulars, the structure, use and operation of the embodiment shown in FIG. 5 are identical to those of the device in FIG. 1, they shall not be further illustrated.

Figure 7:
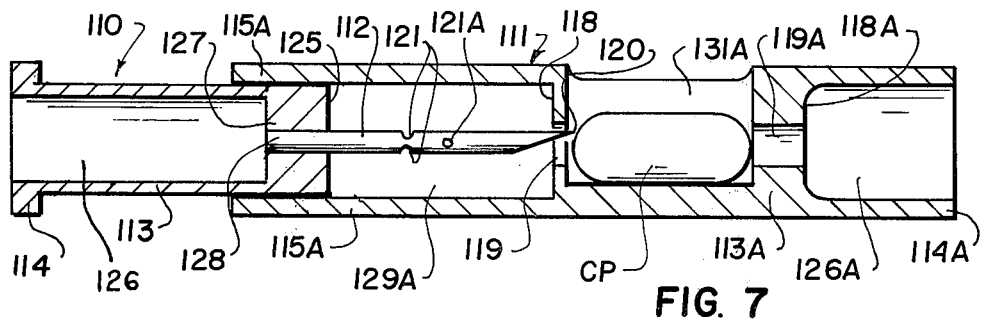
FIG. 7 is an axial sectional view of the device in FIG. 5, showing the capsule in its inserted position.
Figure 8:
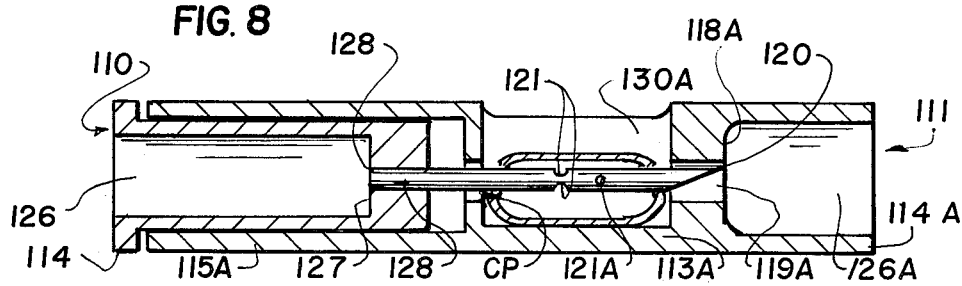
FIG. 8 is a sectional view of the device in FIG. 5, showing the pierced capsule.

The second embodiment of the device according to the invention, illustrated in FIGS. 6 through 8, wherein the elements identical or similar to those of the first embodiment have been designated with the same reference numerals increased by the integer 100, also comprises two separate members 110, 111.

The member 110 consists of a cylindrical body 113 having a recess 126 open at the end 114 and closed at the end 125 by means of an end wall 127 having a centrally-positioned opening 128 which sealingly receives the end of a hollow needle 112 having an open-ended tip 120, a first pair of diametrically opposed holes 121 and a second pair of diametrically opposed holes 121A.

The member 111 comprises a hollow cylindrical body 113A provided with a forward sleeve 115A having a recess 129A of inner diameter slightly larger than the outer diameter of the body 113 of member 110. The sleeve 115A can, therefore, receive the body 113 so that these elements can telescopically slide into each other, like a cylinder-plunger complex.

The hollow body 113A further comprises a chamber 130A having a sidewise opening 131A. The chamber 130A is separated from the recess 129A of the sleeve 115A by a partition wall 118 having a centrally positioned opening 119. A cylindrical recess 126A is separated from the chamber 130A by a partition wall 118A presenting an axial passageway 119A.

The device, thus structured, is used by introducing the capsule CP into the chamber 130A through the sidewise opening 131A as shown in FIG. 7 and then fitting the body 113 into the sleeve 115A of the body 113A and thrusting completely the body into the sleeve in such a way that the hollow needle, after passing through the opening 119, pierces completely the capsule CP, to be eventually received in the passageway 119A. At this moment, the two series of holes 121, 121A on the hollow needle 120 are both inside the capsule CP. In order to inhale the drug in powder form contained in the capsule, one will operate as described in connection with the first embodiment: the user will place the device end 114A in his mouth and inhale the powder contained in the capsule by drawing in air through the opposite end 114. In fact, the drawn in air will enter the capsule through the recess 126, the hollow needle and the holes 121, drag in suspension the powder and leave the holes 121A, the passageway 119A and the recess 126A to pass eventually into the user's mouth.

It is apparent that both the foregoing embodiments achieve the desired results by providing simple, inexpensive devices for the inhalation of drugs in powder form. Because of their low cost, the inhalators of this of this invention can be inexpensively disposed of after a single use thereof.

What is claimed is:

1. A device for the quick inhalation of drugs in powder form by persons suffering from asthma, said drugs being contained in a capsule made of a fairly rigid, pierceable material, comprising: a first and a second hollow cylindrical body, each of said first and second hollow cylindrical bodies having a bore open at both ends, and a hollow piercing element mounted in said bore integral with said body, said hollow piercing element comprising an open-ended small cylinder and a tip mounted at one end of said small cylinder, said tip having apertures extended therethrough for the passage of air, said first hollow cylindrical body including a cylindrical sleeve for receiving the capsule mounted at one end of said bore adjacent said second hollow cylindrical body and telescopically received in said bore of said second hollow cylindrical body, the capsule being mounted in said cylindrical sleeve intermediate said tip of each piercing element, said first and said second hollow cylinder being telescopically moveable toward each other to pass at least one of the respective piercing element relative to the other piercing element between a first position in which the capsule is still in its integral condition and a second position in which both of said piercing elements are passed into the capsule whereby the apertures are inside the capsule, mutually cooperating abutting means for stopping the insertion movement of one of said first and second hollow cylindrical members into the other, a helical spring means connected to each hollow cylindrical body and surrounding each piercing element for resiliently bearing against the capsule and urging said body away from the capsule in said second position, and cooperating means for holding said first and said second hollow cylindrical bodies in said second position counteracting said springs.

2. The device of claim 1, wherein said cooperating means comprises an outer rib on said cylindrical sleeve and a mating groove formed on the inner wall of said second hollow cylindrical body for matingly receiving said outer rib.

3. A device for the quick inhalation of drugs in powder form by persons suffering from asthma, said drugs being contained in a capsule made of a fairly rigid, pierceable material, comprising: a first and a second hollow cylindrical body, each of said first and second hollow cylindrical bodies having a bore open at both ends, and a hollow piercing element mounted in said bore integral with said body, said hollow piercing element comprising an open-ended small cylinder and a tip mounted at one end of said small cylinder, said tip having apertures extended therethrough for the passage of air, said first hollow cylindrical body including a cylindrical sleeve for receiving the capsule mounted at one end of said bore adjacent said second hollow cylindrical body and telescopically receiving in said bore of said second hollow cylindrical body, the capsule being mounted in said cylindrical sleeve intermediate said tip of each piercing element, said first and said second hollow cylinders being telescopically movable toward each other to pass at least one of the respective piercing elements relative to the other piercing element between a first position in which the capsule is still in its integral condition and a second position in which both of said piercing elements are passed into the capsule whereby the apertures are inside the capsule, and cooperating means for holding said first and said second hollow cylindrical bodies to each other in said second position.

4. The device of claim 3, wherein said cooperating means comprises an outer rib on said cylindrical sleeve and a mating groove formed on the inner wall of said second hollow cylindrical body for matingly receiving said outer rib.

* * * * *